United States Patent [19]

Barna

[11] 3,978,212

[45] Aug. 31, 1976

[54] ELECTROLYTE SOLUTIONS CONTAINING MAGNESIUM AND FREE BICARBONATE IONS

[75] Inventor: Bohdan Barna, Pickering, Canada

[73] Assignee: Chemo Drug Company, Weston, Canada

[22] Filed: Dec. 13, 1974

[21] Appl. No.: 532,542

[30] Foreign Application Priority Data

Dec. 19, 1973   Canada ................................. 188504

[52] U.S. Cl. .................................. 424/156; 424/154
[51] Int. Cl.$^2$ ................... A61K 33/06; A61K 33/10
[58] Field of Search ............................ 424/156, 154

[56] References Cited
UNITED STATES PATENTS 3,878,664   4/1975   Zinke ................................. 53/22 R

OTHER PUBLICATIONS

Soine et al., Rogers' Inorganic Pharmaceutical Chemistry (1957), sixth edition, p. 379.

*Primary Examiner*—Sam Rosen
*Attorney, Agent, or Firm*—Richard J. Hicks

[57] ABSTRACT

An aqueous electrolyte solution containing magnesium cations and bicarbonate anion which contains carbon dioxide gas dissolved in the solution as carbonic acid in an amount up to the saturation point of the solution so that it can be terminally sterilized in a sealed container to produce a clear solution without precipitated water insoluble magnesium compounds, which is especially suitable for parenteral injection.

18 Claims, No Drawings

ELECTROLYTE SOLUTIONS CONTAINING MAGNESIUM AND FREE BICARBONATE IONS

The present invention relates to electrolyte solutions containing magnesium cation and bicarbonate anion which are terminally sterilizable without precipitation of insoluble magnesium compounds. Such precipitates render the solutions useless for parenteral use.

The use of parenterally injectable electrolyte solutions is well established in lower animal and human therapy. The principal uses are probably post surgically for maintenance therapy and to replace electrolytes lost through vomiting, aspiration, hemorrhage, excessive sweating and other causes. In most instances the solutions principally contain the inorganic cations of sodium, potassium, calcium and/or magnesium and anions such as chloride, bicarbonate and/or monophosphate in order to approximate the composition of the body extra cellular fluid. For instance the inorganic anionic and cationic composition of extra-cellular fluid and various known parenteral electrolyte solutions are shown in Table I on page 2. The solutions of the present invention may be administered orally for the replacement of water and electrolyte in cases of dehydration or electrolyte loss which do not require parenteral therapy. The solutions may also be administered subcutaneously, intradermally and in other ways.

|  | Cations (mEq./L.) | | | | Anions (mEq./L.) | | | |
|---|---|---|---|---|---|---|---|---|
|  | $Na^+$ | $K^+$ | $Ca^{++}$ | $Mg.^{++}$ | $Cl^-$ | $HCO_3^-$ | $HPO_4^=$ | $H_2PO_4^-$ |
| Extracellular Fluid | 135–147 | 4.1–5.7 | 4.5–6.0 | 1.5–3.0 | 98–106 | 25–31 | 1.2–3 | — |
| Electrolyte Solutions | | | | | | | | |
| Normal Saline | 154 | — | — | — | 154 | — | — | — |
| Ringer's Solution | 145 | 4 | 4.5 | — | 155.5 | — | — | — |
| Lactated Ringer's Solution | 130 | 4 | 3 | — | 109 | 28 | — | — |
| Darrow's[1] Solution | 122 | 35 | — | — | 104 | 53 | — | — |
| Ordway's Solution | 26 | 27 | — | — | 53 | — | — | — |
| Butler's Solution | 55 | 23 | — | 5 | 45 | 26 | 12 | — |
| Tyrode's Solution | 145 | 2.7 | 0.9 | 0.5 | 138.5 | 12 | — | 0.4 |
| Locke Ringer's Solution[2] | 160 | 5.6 | 1.0 | 1.0 | 164 | 6.0 | — | — |

[1]Also contains 53 mEq./L. Lactate
[2]Also contains 0.5 gm/L dextrose

There are numerous other solutions with varying amounts of the inorganic anions and cations, but in general in milli-equivalents per liter sodium is between 20 and 160; potassium 1 to 40; calcium 0.5 to 10; magnesium 0.5 to 10; chloride 20 to 170; bicarbonate 1 to 60; monophosphate 0.5 to 20 and/or biphosphate 0.1 to 1.0.

As can be seen from Table I, few of the solutions contain magnesium cation and yet it is an important component of extra-cellular fluid in humans and in lower animals particularly mammals. It is believed that magnesium and other alkali metal and alkaline earth metal cations have a significant effect in providing osmotic pressure for electrolyte and anion transport across the cell membrane into the cells.

A difficult problem results with solutions incorporating magnesium in the presence of bicarbonate when they are terminally sterilized which involves heat sterilization in a sealed container for a sufficient length of time to make certain that the solutions are sterile. Commercially this involves the use of steam heating in an autoclave under pressure (for instance 30 pounds gauge) for a long period of time (usually 30 minutes to 2 hours) at a temperature of 150°C. In each instance a magnesium compound precipitates from solution. For this reason microfiltration into sterile containers has been used for the sterilization of such solutions which is much more expensive and time consuming. Heat sterilization is well known and discussed in Kirk-Othmer, Encyclopedia of Chemical Technology, Volume 18 (2nd Edition 1969), pages 805 to 829.

It is therefore an object of the present invention to provide a novel method for producing novel parenterally injectable electrolyte solutions containing magnesium cation and bicarbonate anion which can be terminally sterilized. These and other objects will become increasingly apparent by reference to the following description.

One aspect of the present invention is in the method for preparing a clear, aqueous electrolyte solution comprising bicarbonate anion and magnesium cation at ambient temperatures which can be sterilized by heating in a sealed container at elevated temperatures, which comprises providing carbon dioxide gas dissolved in the solution as carbonic acid in an amount up to about the saturation point of the solution and sufficient to prevent the formation and precipitation of water insoluble magnesium compounds during terminal sterilization. Preferably, the resulting pH of the sterilized solution is not less than about 6.0.

The present invention also relates to a composition which comprises (a) a clear aqueous electrolyte solution comprising magnesium cation and bicarbonate anion; and (b) carbon dioxide gas dissolved in the solution as carbonic acid in an amount up to about the saturation point of the solution so as to be terminally sterilizable at elevated temperatures in a sealed container to leave a clear solution without precipitated water insoluble magnesium compounds and preferably having a sterilized pH of not less than about 6.0. Further, the present invention relates to an article of manufacture in a sealed container, in the form of a clear terminally sterilized solution which comprises (a) magnesium cation and bicarbonate anion dissolved in a clear parenterally injectable aqueous electrolyte solution; and (b) between 0.05 and 1.8 milliequivalents of carbon dioxide dissolved in the solution as carbonic acid at ambient temperatures and pressures per milliequivalent of bicarbonate anion, the solution being sterilizable in the sealed container to produce a clear solution without precipitated water insoluble magnesium compounds.

The bicarbonate anion forms a buffer system in blood with carbonic acid such that acidic hydrogen cations ($H^+$) are neutralized by the basic bicarbonate anions ($HCO_3^-$) and hydroxyl ions ($OH^-$) are neutralized by carbonic acid to form bicarbonate and water. The "normal" pH is considered about 7.4 although in fact for venous blood it is closer to a pH of 7.1 because of dissolved carbon dioxide as carbonic acid. The body maintains a ratio of bicarbonate to carbonic acid of about 20:1. In milliequivalents per liter (mEq./L.) this averages about 1.35 for carbonic acid and 27 for bicarbonate. The respiratory system regulates the ratio by the preservation or elimination of carbon dioxide. In acidosis the pH of the blood is lowered because of reaction with bicarbonate. This actuates greater respiration of carbon dioxide from carbonic acid which restores the decreased 20:1 ratio. In alkalosis, such as from vomiting where hydrochloric acid from the stomach is lost, this increases the relative amount of base. In this instance, the kidney is activated to excrete more bicarbonate to restore the increased 20:1 ratio. All of these characteristics are well known in the prior art as disclosed for instance in Muntwyler, Edward, *Water and Electrolyte Metabolism And Acid Base Balance*, the C. V. Mosby Company, St. Louis, Missouri (1968) and Brooks, Steward M., *Basic Facts of Pharmacology* W. B. Saunders Company, Philadelphia, Pennsylvania (2nd Edition 1963) in Chapter VII.

The chemistry of blood or aqueous electrolyte solutions of bicarbonate and carbonic acid is that the two are in equilibrium as follows:

   1

At ambient temperatures and pressures this equilibrium is very much to the left which accounts for the 20:1 ratio of bicarbonate to carbonic acid. It has been found that at the elevated temperatures and extended times used for terminal sterilization of electrolyte solutions in sealed containers that this equilibrium was transferred much further to the right. As can be seen from the table at page 1100 of Lange's Handbook of Chemistry (10th Edition 1967), the solubility of carbon dioxide in water drops vary markedly with increase in temperature.

In the sealed containers used for storage and handling of parenteral electrolyte solutions, a space is preferably provided above the solution which is filled with air usually at a pressure less than atmospheric at ambient temperatures. This vacuum serves as a check of the sterility of the solution since bacteria generate gases which eliminate the vacuum.

Where no magnesium cations are present in the electrolyte solution, terminal sterilization is easily achieved. When magnesium cations were provided dissolved in the solutions, the resulting solutions were clear until they were terminally sterilized and then a precipitate was formed. It was found that this precipitate was a magnesium compound insoluble in water and is principally highly insoluble magnesium hydroxide (brucite). It is now believed that at elevated temperatures carbonic acid is going out of solution as carbon dioxide gas and that the remaining solution becomes much more basic in hydroxyl ion which causes the formation of magnesium hydroxide which precipitates from solution according to the reaction:

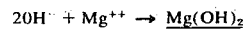

Unexpectedly it was found that the formation of a magnesium precipitate in this manner could be prevented by incorporating carbon dioxide gas dissolved in th solutions. The carbon dioxide is believed to repress the formation of carbonic acid by equilibrium reaction I during sterilization and based upon well known concentration principles drives the reaction to the left. Upon heating the bicarbonate does not form a significantly increased amount of carbonic acid per reaction I since there is a large excess of carbon dioxide gas already present in the solution. In this manner clear terminally sterilized solutions can be prepared.

The carbon dioxide is preferably provided by bubbling through a tube in the solution. This is most conveniently done at ambient temperatures (26°C) although it will be appreciated that by lowering the temperature of the solution more carbon dioxide will dissolve in the solution or the introduction can be faster. At elevated temperatures from ambient the reverse is true. Also a metered amount of the gas can be provided in the space above the closed container at ambient, reduced or elevated pressures. Further still, solid carbon dioxide can be provided in the solution which is then provided in a closed container. Various other means for providing the carbon dioxide in solution at the elevated temperatures can be used such as by heating formaldehyde or paraformaldehyde in solution to form carbon dioxide and water.

The pH of the resulting sterile solution should preferably not be less than about 6.0 and more preferably be between 6.0 and 7.0. The required pH will determine the amount of carbon dioxide which should be incorporated and the pH is easily determined.

The magnesium cation is provided in the solution in the form of water soluble, physiologically acceptable salts including inorganic and organic salts. Such salts are for instance, magnesium chloride, magnesium sulfate, magnesium gluconate, magnesium acetate, and magnesium lactate. The bicarbonate anion is usually provided in the solution as an alkali or alkaline earth metal salt preferably potassium or sodium salt although calcium or magnesium salts can be used. The other anions and cations are usually provided by sodium chloride, calcium chloride, potassium chloride, sodium monophosphate and sodium biphosphate.

The electrolyte solutions may also be combined with plasma expanders such as Dextran to enhance their utility, or may be used as a base for amino acids, carbohydrates, vitamins, additional minerals and other desired additives for intravenous alimentation or hyperalimentation. Only slight further modification can provide a liquid elemental highly nutritive preparation useful for oral hyperalimentation in those cases where freedom from indigestable matter is desirable.

Organic molecules, such as dextrose and fructose, may be incorporated into the solution to provide energy for cell metabolic processes. Lactate anion is believed to be converted to bicarbonate in the liver to correct acidosis; however, in certain diseases this metabolism does not take place such as circulatory insufficiency, hepatic glycogenesis and spontaneous lactic acidemia. Bicarbonate also appears to be better than lactate with diabetes mellitus and the acidosis of salicylate poisoning as discussed by Muntwyler.

It has been found that between 0.05 and 1.8 milliequivalents carbon dioxide per milliequivalent bicarbonate ion is preferred depending upon the amount of magnesium ion. A millimole of carbon dioxide is considered to produce one milliequivalent of carbonic acid. The amount of carbon dioxide dissolved will preferably be that necessary to provide a pH of not less than about 6.0 in combination with the bicarbonate anion and the magnesium cation. Preferably the solution contains between about 1 and 100 milliequivalents per liter of bicarbonate anion and between 0.1 and 10 milliequivalents magnesium cation per liter (millimoles per liter divided by valence of 2).

Generally the solutions have an osmolarity of between about 250 and 310 milliosmols per liter where 1 milliosmol per liter equals 1 milliequivalent per liter. Normally osmolarity is determined in an osmometer by reference to the depression of the freezing point of the solution and by providing a correction for the ionic character of the solution. The milliosmolarity is the sum of the milliosmols of solutes in solution and represents the osmotic driving force, principally from sodium, potassium, calcium and magnesium cations, to provide water and other ions intracellularly.

The foregoing description is illustrated by the following Example wherein solutions are compared with the added carbon dioxide in the manner of the present invention and then without.

EXAMPLE

Six (6) liters of solution were prepared according to the following formula:

| NaCl | 39.6 Gm. | 6.6 Gm/L |
|---|---|---|
| $MgSO_4 \cdot 7H_2O$ | 7.4 Gm. | 1.21 Gm/L |
| K Cl | 6.25 Gm. | 1.02 Gm/L |
| $NaHCO_3$ | 9.1 Gm. | 1.51 Gm/L |
| $EDTA \cdot Na_2$ | 0.9 Gm. | 0.15 Gm/L |
| $H_2O$ distilled to | 6.0 liters | |

Concentration Solutes

| sodium | 131 |
|---|---|
| potassium | 14 |
| magnesium | 2.5 |
| bicarbonate | 18 |
| chloride | 127 |
| sulfate | 2.5 |
| milliosmolarity | 300 mOsm/L |

The solution was prepared in the conventional manner and filtered. Half of the solution (3 liters) was filled into 500 ml., transfusion bottles. The remaining 3 liters was treated with pure $CO_2$ gas for 30 minutes by bubbling it into solution at room temperatures (26°C) and atmospheric pressure (760 torr), then filled into 500 ml., transfusion bottles. Two bottles from each half were then autoclaved at 15 lbs., pressure for 30 minutes, 1 hour and 2 hours respectively. The bottles were placed in a cold room overnight (4°C.) to accelerate any precipitation which might take place, and examined the following morning. All six bottles without carbon dioxide contained a crystalline precipitate, whereas all of the bottles containing solution treated with carbon dioxide were crystal clear and entirely free of any particulate matter. The solution without carbon dioxide has a pH range of 7.4 to 7.45 and a measured osmolarity (mOsm/L) of 276 to 278. The carbon dioxide containing solution had a pH range of 6.05 to 6.10 and a measured osmolarity of 298 to 301. The osmolarity of blood plasma is 300 to 303 and the pH of arterial plasma is 7.35 to 7.45 as indicated in Muntwyler.

The higher osmolarity of the solutions of the present invention is contributed by the carbon dioxide and corresponds well to the calculated milliosmols based upon pure water at 26°C and 760 torr of 32 milliequivalents or milliosmols per liter which is up to the saturation point.

The very small amount of sodium EDTA is usually provided in the solution to chelate magnesium so as to insure that it does not precipitate from solution upon standing for long periods. It is also used for this purpose with calcium cations. However, in the compositions of the present invention such chelating agents are not essential and can be eliminated. Indeed such elimination may be highly desirable in intravenous applications to avoid complexing of blood calcium.

I claim:

1. In the method for preparing a clear, aqueous electrolyte solution comprising bicarbonate anion and magnesium cation at ambient temperatures, the improvement which comprises:

providing carbon dioxide gas dissolved in the solution as carbonic acid in amounts up to about the saturation point of the solution and sufficient to prevent the formation and precipitation of water insoluble magnesium compounds, and thereafter terminally sterilizing said solution by heating in a sealed container at elevated temperatures.

2. The method of claim 1 wherein carbon dioxide gas is provided by being bubbled into the solution.

3. The method of claim 1 wherein carbon dioxide is provided by adding solid carbon dioxide to the solution which sublimates to carbon dioxide gas and dissolves in the solution.

4. The method of claim 1 wherein the resulting pH of the sterilized solution is not less than about 6.0.

5. A composition in the form of a clear sterile solution which comprises:
   a. a clear aqueous electrolyte solution comprising magnesium cation and bicarbonate anion; and
   b. carbon dioxide gas dissolved in the solution as carbonic acid in an amount up to about the saturation point of the solution so as to be terminally sterilizable at elevated temperatures in a sealed container to leave a clear solution without precipitated water insoluble magnesium compounds.

6. A composition as claimed in claim 5 having a sterilized pH of not less than about 6.0.

7. The composition of claim 5 wherein a space is provided above the solution in the sealed container which is filled with carbon dioxide gas and which at ambient temperatures is under slightly reduced pressures from atmospheric after sterilization.

8. The composition of claim 5 wherein the bicarbonate anion is provided by sodium bicarbonate.

9. The composition of claim 5 wherein the solution approximates the inorganic anion and cation composition of normal human extracellular fluid.

10. The composition of claim 5 wherein the solution has a pH of between 6 and 7.

11. The composition as claimed in claim 5 wherein said clear aqueous electrolyte solution is parenterally injectable.

12. An article of manufacture, in a sealed container, which comprises:
   a. magnesium cation and bicarbonate anion dissolved in a clear aqueous electrolyte solution; and
   b. between 0.05 and 1.8 milliequivalents of carbon dioxide dissolved in the solution, up to the saturation point thereof, as carbonic acid at ambient temperatures and pressures per milliequivalent of bicarbonate anion, the solution being terminally sterilizable in said sealed container to produce a clear solution without precipitated water insoluble magnesium compounds.

13. The article of claim 12 wherein the bicarbonate anion is provided by sodium bicarbonate.

14. The article of claim 12 wherein the solution approximates the inorganic anionic and cationic composition of normal human extracellular fluid.

15. The article of claim 12 wherein the solution has a pH between 6 and 7.

16. The article of claim 12 which contains between about 1 and 100 milliequivalents per liter of bicarbonate anion.

17. The article of claim 12 which contains between about 1 and 100 milliequivalents per liter of bicarbonate anion and between about 0.1 and 10 milliequivalents of magnesium cation per liter.

18. The article as claimed in claim 12, wherein said clear aqueous electrolyte solution is parenterally injectable.

* * * * *